(12) United States Patent
Kawase et al.

(10) Patent No.: US 7,019,167 B2
(45) Date of Patent: Mar. 28, 2006

(54) PROCESS FOR PRODUCING ALKANEDICARBOXYLIC ACID

(75) Inventors: Masatsugu Kawase, Nobeoka (JP); Yasuhiro Murozono, Nobeoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 142 days.

(21) Appl. No.: 10/470,163

(22) PCT Filed: Jan. 24, 2002

(86) PCT No.: PCT/JP02/00513

§ 371 (c)(1),
(2), (4) Date: Jul. 24, 2003

(87) PCT Pub. No.: WO02/059071

PCT Pub. Date: Aug. 1, 2002

(65) Prior Publication Data
US 2004/0073061 A1   Apr. 15, 2004

(30) Foreign Application Priority Data
Jan. 25, 2001   (JP) .............................. 2001-016819

(51) Int. Cl.
*C07C 51/245* (2006.01)
(52) U.S. Cl. ...................... 562/528; 562/530; 562/539; 562/540
(58) Field of Classification Search ................ 562/512, 562/528, 529, 530, 590, 597
See application file for complete search history.

(56) References Cited

U.S. PATENT DOCUMENTS 3,290,367 A * 12/1966 White et al. ................. 562/530
3,359,308 A    12/1967 Sampson, Jr.

FOREIGN PATENT DOCUMENTS

| FR | 1428374 | * | 5/1966 |
| GB | 1511438 A | | 5/1978 |
| JP | 43-19529 B1 | | 8/1967 |
| JP | 43-19529 B | | 8/1968 |
| JP | 4319529 | * | 8/1968 |
| JP | 48-21088 B | | 6/1973 |
| JP | 61-257940 A | | 11/1986 |

OTHER PUBLICATIONS

W.J. van Asselt et al., Rec. Tra. Chem., vol. 82, 1963, pp. 51-67.
W. J. van Asselt et al., Rec. Tra. Chem., vol. 82, 1963, pp. 429-437.
W. J. van Asselt et al., Rec. Tra. Chem., vol. 82, 1963, pp. 438-449.

* cited by examiner

*Primary Examiner*—Johann Richter
*Assistant Examiner*—Karl Puttlitz
(74) *Attorney, Agent, or Firm*—Birch, Stewart, Kolasch & Birch, LLP

(57) ABSTRACT

A method for manufacturing an alkanedicarboxylic acid by oxidizing cycloalkanol and/or cycloalkanone with an aqueous solution of nitric acid, which comprises using an adiabatic reactor comprising a feed nozzle enabling to feed cycloalkanol and/or cycloalkanone at a linear velocity not lower than $8\times10^{-2}$ m/sec and a mixing apparatus.

8 Claims, 2 Drawing Sheets

PROCESS FOR PRODUCING ALKANEDICARBOXYLIC ACID

This application is the national phase under 35 U.S.C. § 371 of PCT International Application No. PCT/JP02/00513 which has an International filing date of Jan. 24, 2002, which designated the United States of America.

TECHNICAL FIELD

This invention relates to a method for manufacturing an alkanedicarboxylic acid by oxidizing cycloalkanol and/or cycloalkanone with nitric acid. More specifically, this invention relates to a method for manufacturing an alkanedicarboxylic acid using an adiabatic reactor, wherein the yield of alkanedicarboxylic acid generated is high, irrespective of temperature of said adiabatic reactor.

BACKGROUND ART

It has been conventionally known that cycloalkanol and/or cycloalkanone can be oxidized with nitric acid to an alkanedicarboxylic acid at elevated temperatures. There is also a known method for manufacturing an alkanedicarboxylic acid by oxidizing cycloalkanol and/or cycloalkanone with nitric acid using an adiabatic reactor. JP-B-43-19529, for example, discloses a continuous one-step manufacturing method for an alkanedicarboxylic acid by oxidizing cycloalkanol, cycloalkanone or cycloalkylamine and/or ω-hydroxylalkane dioic acids having at least 4 carbon atoms and lactones thereof or tetrahydrofuran with nitric acid at elevated temperatures in a recirculating system, wherein starting materials are vigorously mixed with 80 to 400 times the amount in volume of 40 to 70% nitric acid. The amount of nitric acid is adjusted so that the reaction temperature during the reaction does not exceed 25° C. The reaction proceeds at 45 to 90° C. under a normal pressure or a pressurized condition, and the reaction mixture coming out from a reaction zone is separated from nitrogen oxide after 4 minutes or less of residence time. The concentration of nitric acid is raised again up to the concentration nearly equivalent to the concentration in the reaction zone by evaporating water from the reaction mixture, and an alkanedicarboxylic acid is separated from a part of the reaction mixture by an usual method. The mother liquid is added to the remaining part of the reaction mixture, and the thus joined mixture is vigorously mixed with fresh starting materials and returned to the reaction zone. The disclosure describes that the mixing of nitric acid and starting materials (i.e. cycloalkanol, cycloalkanone or cycloalkylamine and/or ω-hydroxylalkane dioic acids having at least 4 carbon atoms, lactones thereof or tetrahydrofuran) is preferably performed within as short a time as possible when nitric acid (i.e. nitric acid sent to a circulation line and/or nitric acid freshly fed) is introduced into the reaction zone after having been mixed with the starting materials. The disclosure describes that it is preferable to mix them so that the starting materials are dissolved into a transparent state within 5 seconds at the latest using, for example, an injector, a mixing nozzle or a turbine mixer. Particularly, in the case of oxidation of cyclohexanol and cyclohexanone, it is disclosed to make an effort to obtain a transparent solution within 0.05 to 0.1 seconds after mixing. It describes that the reason for this is that a longer mixing time causes a local elevation of temperature in the reaction zone, resulting in a decrease in yield of an alkanedicarboxylic acid. However, even with the mixing time described in JP-B-43-19529, a yield of an alkanedicarboxylic acid is not necessarily high. This means that the mixing time defined in JP-B-43-19529 is not adequate.

It is also known in other literature that a higher temperature lowers a yield of adipic acid in oxidizing cyclohexanol and/or cyclohexanone with nitric acid to obtain adipic acid. For example, "Preparation of adipic acid by oxidizing cyclohexanol and cyclohexanone with nitric acid", W. J. VAN ASSELT and D. W. VAN KREVELEN, Rec. Tra. Chem., 82, 51–67, 429–437, 438–449 (1963) shows that yield of adipic acid lowers at a high temperature, in particular, not lower than 60° C., even in the presence of a copper catalyst, from results of a batch oxidation reaction test using a cylindrical vessel equipped with a magnetic stirrer and a cooling jacket.

Therefore, in JP-B-43-19529, a reaction is recommended to proceed at the temperature of 45 to 90° C. under a normal pressure or a pressurized condition, though a residence time or a mixing time is regulated within an extremely short time. Further, examples in JP-B-43-19529 clearly describes an outlet temperature to be 70° C.

On the other hand, it is also clear that a concentration of nitric acid required for obtaining the same yield of adipic acid increases with lowering of temperature based on a calculation using the reaction rate of cyclohexanol or cyclohexanone to adipic acid obtained in the same literature; "Preparation of adipic acid by oxidation of cyclohexanol and cyclohexanone with nitric acid", W. J. VAN ASSELT and D. W. VAN KREVELEN, Rec. Tra. Chem., 82, 51–67, 429–437, 438–449 (1963).

This means that, in conventional technology, lowering the temperature requires a higher amount of nitric acid in the oxidation reaction to give an increased yield of adipic acid. That is, the method shown in the above described JP-B-43-19529 has a problem in that a high amount of nitric acid is consumed due to oxidizing cyclohexanol and/or cyclohexanone with nitric acid at low temperatures such as 45 to 90° C.

JP-B-48-21088 describes a method for reducing the amount of nitric acid consumed. Said official gazette discloses a method for converting cycloalkanol and/or cycloalkanone to an alkanedicarboxylic acid by a liquid-phase oxidation with nitric acid, wherein only small amounts of nitric acid are essentially consumed. More specifically, it discloses a method for manufacturing an alkanedicarboxylic acid by a liquid-phase oxidation of reaction components selected from the group consisting of cycloalkanol and cycloalkanone with nitric acid, which has improved the reduction in the amount of nitric acid consumed, wherein said reaction components are contacted with nitric acid in the presence of a copper-vanadium catalyst at 90 to 140° C., at least a part of the reaction mixture comprising 0.30 to 0.60% by weight of oxidized copper, 0.01 to 0.50% by weight of oxidized vanadium and a reduction product of nitric acid having an average oxygen/nitrogen ratio larger than 0.5 is circulated, wherein a weight ratio of circulation flow to reaction components is maintained at 200 to 1300 and a product of said weight ratio and the concentration of the oxidized vanadium is maintained at 30 to 60, followed by recovering said alkanedicarboxylic acid. Circulation here means a circulation only in a reaction system, which is different from "total circulation flow" of an aqueous nitric acid solution of the present invention described below. In this description, this circulation is defined as "circulation flow in reaction system".

Furthermore, JP-B-48-21088 describes that a suitable mixing apparatus such as draft-tube-mixer may be used to reduce the difficulty of mixing of the flow by mixing the incoming flow of the cycloalkanol and/or cycloalkanone with the circulation flow in the reaction system from the reaction apparatus. This method, however, requires that the weight ratio of the circulation flow in the reaction system of the reaction components is set at an extremely high level such as 200 to 1300. A large volume of circulation flow in the reaction system requires a large pump capacity to ensure such a large circulation volume as well as pipe lines and a reactor considering the pressure loss, and is thus disadvantageous with respect to equipment cost and proportional cost of power.

As listed above, although various methods for oxidizing cycloalkanol and/or cycloalkanone to an alkanedicarboxylic acid with nitric acid are known, they require maintaining a reaction zone at a temperature not higher than 90° C. or require an extremely large amount of circulation flow of nitric acid in the reaction system in the case of temperatures above 90° C., to improve the yield of alkane dioic acid. In addition, temperatures in the reaction zone not higher than 90° C. has problems such as a large amount of nitric acid consumption, a large volume of air in a stripper tower and a large volume of total circulation flow of an aqueous solution of nitric acid containing the alkanedicarboxylic acid product which is wholly circulating within the system, thus resulting in increased loads of a crystallizer and a concentration tower. Temperatures above 90° C. also has a problem of an extremely large amount of nitric acid circulation flow in a reaction system to maintain a yield of the alkanedicarboxylic acid.

DISCLOSURE OF THE INVENTION

An object of the present invention is to solve problems of the above conventional methods and to provide a method for manufacturing an alkanedicarboxylic acid by oxidizing cycloalkanol and/or cycloalkanone with nitric acid, using an adiabatic reactor, which enables improved yields of alkanedicarboxylic acid without increasing the circulation flow of nitric acid in reaction system more than is required, as well as enabling the reduction in the amount of nitric acid required, in the air volume in a stripper tower, in a total circulation flow of an aqueous nitric acid solution and in the loads of a crystallizer and a concentration tower, irrespective of the temperature in said adiabatic reactor.

In oxidizing cycloalkanol and/or cycloalkanone with nitric acid to obtain an alkanedicarboxylic acid, if the outlet temperature of said adiabatic reactor can be raised, not only is there an advantage in suppressing the amount of nitric acid to be used as described above, but also in reducing the air volume to be fed into a stripper tower as described in said JP-B-43-19529 can be obtained, because a concentration of alkanedicarboxylic acid formed in a reaction liquid at a reactor outlet can be increased.

There is another advantage coming from the case where an outlet temperature of an adiabatic reactor can be raised. Generally, in a process to obtain an alkanedicarboxylic acid by oxidizing cycloalkanol and/or cycloalkanone with nitric acid, an aqueous solution of nitric acid containing an alkanedicarboxylic acid product contains a large excess of nitric acid which is more than required for the reaction. Therefore, after separating an alkanedicarboxylic acid product from an aqueous solution of nitric acid containing the alkanedicarboxylic acid formed by crystallization or distillation, the excess nitric acid is concentrated and recovered for reuse in circulation. In this description, this is defined as "total circulation" of an aqueous solution of nitric acid.

The present inventor found by an enthusiastic study that the above problems can be solved by using a specific method for mixing cycloalkanol and/or cycloalkanone with nitric acid, as a method for improving the yield of alkanedicarboxylic acid without increasing both volumes of circulating nitric acid in a reaction system and total circulation flow, irrespective of the temperature in said adiabatic reactor, in a method for manufacturing an alkanedicarboxylic acid by oxidizing cycloalkanol and/or cycloalkanone with an aqueous solution of nitric acid, and finally completing the present invention.

Thus, the first aspect of the present invention is a method for manufacturing an alkanedicarboxylic acid by oxidizing cycloalkanol and/or cycloalkanone with an aqueous solution of nitric acid, which comprises using an adiabatic reactor comprising a feed nozzle enabling to feed said cycloalkanol and/or cycloalkanone at a linear velocity of not lower than $8 \times 10^{-2}$ m/sec and mixing apparatus.

The second aspect of the present invention is a method according to the first aspect of the present invention, wherein an outlet temperature of said adiabatic reactor is above 90° C.

The third aspect of the present invention is a method according to the first or the second aspect of the present invention, wherein a fluid comprising said aqueous solution of nitric acid, a reaction product from said cycloalkanol and/or cycloalkanone and said aqueous solution of nitric acid and unreacted portion of said cycloalkanol and/or cycloalkanone, has a standard deviation of not higher than 1.5° C. in a temperature profile in a radial direction of said adiabatic reactor at the position where said fluid flows out from an outlet of said mixing apparatus by 2.5 sec.

The fourth aspect of the present invention is a method according to the first or the second aspect of the present invention, wherein a temperature profile in a radial direction of said adiabatic reactor has a standard deviation not higher than 1.5° C., at the position apart from said mixing apparatus by the same distance as the radius of said adiabatic reactor.

The fifth aspect of the present invention is a method according to any one of the first to the fourth aspects of the present invention, wherein a fluid comprising said aqueous solution of nitric acid, a reaction product from said cycloalkanol and/or cycloalkanone and said aqueous solution of nitric acid and an unreacted portion of said cycloalkanol and/or cycloalkanone, has a standard deviation of not higher than 1.5° C. in a temperature profile in a radial direction of said adiabatic reactor at the position where said fluid flows out from an outlet of said mixing apparatus by 2.5 sec, and also a temperature profile in a radial direction of said adiabatic reactor has a standard deviation of not higher than 1.5° C., at the position apart from said mixing apparatus by the same distance as the radius of said adiabatic reactor.

The sixth aspect of the present invention is a method according to any one of the first to the fifth aspects of the present invention, wherein said aqueous solution of nitric acid is the one which is returned to the reactor after the steps of separating nitrogen oxide, dinitrogen oxide, nitrogen dioxide and nitrous acid from the reaction mixture coming out from said adiabatic reactor after the nitric acid oxidation reaction, then concentrating said reaction mixture until obtaining a concentration of nitric acid nearly equivalent to the concentration of nitric acid at an inlet of reactor by evaporating water formed in said adiabatic reactor from said reaction mixture, separating said alkanedicarboxylic acid from a part of concentrated said reaction mixture, concentrating nitric acid in the mother liquid in another concentrating system, joining said mother liquid and the remaining part of said concentrated reaction mixture together, and mixing the joined mixture with a fresh aqueous nitric acid solution.

The seventh aspect of the present invention is a method according to any one of the first to the sixth aspects of the present invention, wherein said cycloalkanol and/or cycloalkanone is cyclohexanol and/or cyclohexanone and said alkanedicarboxylic acid to be manufactured is adipic acid.

According to the method of the present invention, a yield of an alkane dioic acid can be improved without increasing both volumes of circulation in a reaction system and total circulation flow, irrespective of temperature in said adiabatic reactor, because of specifying the mixing state of cycloalkanol and/or cycloalkanone with nitric acid. Furthermore, according to the method of the present invention, an amount of nitric acid required can be saved, and an air volume in a stripper tower and loads of a crystallizer and a concentration tower can also be reduced.

BEST MODE FOR CARRYING OUT THE INVENTION

Cycloalkanol in the present invention includes cyclopentanol, cyclohexanol, methylcyclohexanol, cyclooctanol and cyclododecanol, and cycloalkanon includes cyclohexanone, methylcyclohexanone and cyclododecanone.

The above compounds may be used alone or in combination as raw materials. In the present invention, cyclohexanol is preferable as a cycloalkanol and cyclohexanone is preferable as a cycloalkanone. A mixture of cyclohexanol and cyclohexanone may be used as raw materials and cyclohexanol may also be used by alone as a raw material. These raw materials may remain as unreacted cycloalkanol and/or cycloalkanone after the reaction.

An aqueous solution of nitric acid in the present invention means an aqueous solution with a nitric acid concentration of 10 to 70%, preferably an aqueous solution with a nitric acid concentration of 40 to 65%, and more preferably an aqueous solution with a nitric acid concentration of 50 to 65%. Here, concentration of nitric acid means a concentration of nitric acid obtained purely from amounts of $HNO_3$ and $H_2O$ excluding an alkanedicarboxylic acid as a reaction product and unreacted cycloalkane and/or cycloalkanol, that is, $[HNO_3/(H_2O+HNO_3)]$.

An alkane dioic acid in the present invention includes succinic acid, glutaric acid, adipic acid and dodecane dioic acid, and adipic acid obtained from cyclohexanol and/or cyclohexanone as a raw material is preferable.

In the present invention, a mixing method for the above described cycloalkanol and/or cyclohexanone with an aqueous solution of nitric acid is important.

That is, in one mixing method of the present invention, said cycloalkanol and/or cycloalkanone is fed using a feed nozzle enabling to feed said cycloalkanol and/or cycloalkanone at a linear velocity not lower than $8\times10^{-2}$ m/sec. Another mixing method of the present invention is to use a mixing apparatus to mix an aqueous solution of nitric acid with cycloalkanol and/or cyclohexanone.

Figure 1:
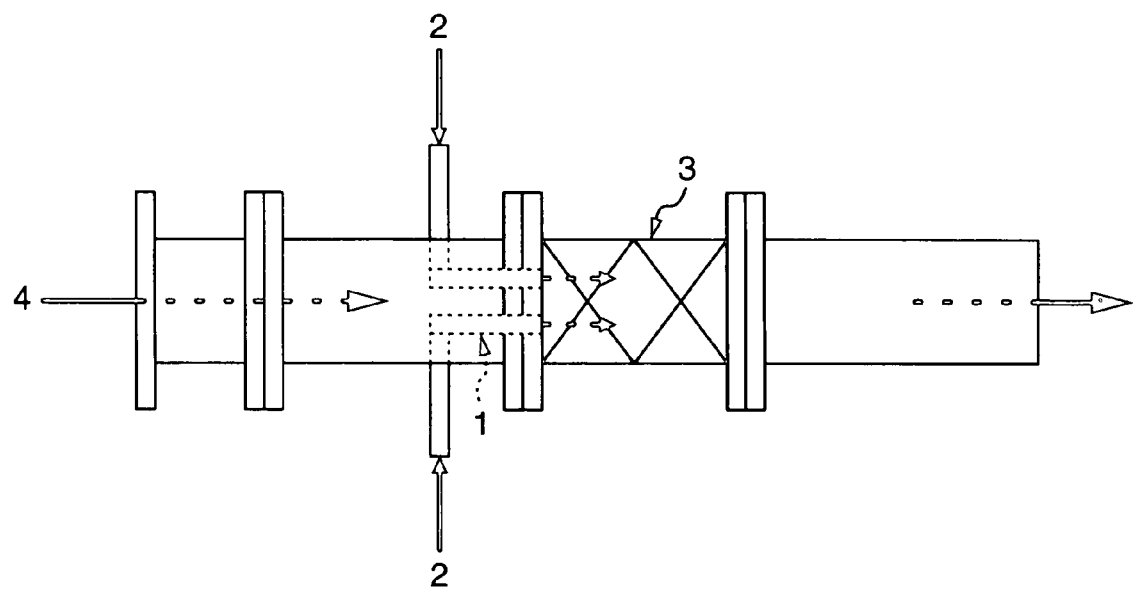
FIG. 1 is a schematic diagram of mixing apparatus in a method of the present invention.

FIG. 1 shows an example of said feed nozzle 1 for cycloalkanol and/or cyclohexanone. Though two sets of feed nozzle 1 are shown in FIG. 1, the nozzle may be one set or three or more sets. The feed nozzle may be a single tube having one hole at the end, or have two or more holes at the end. The important thing is the linear velocity of cycloalkanol and/or cycloalkanone 2 to be fed from said feed nozzle.

The linear velocity of cycloalkanol and/or cycloalkanone 2 in the present invention means a linear velocity of cycloalkanol and/or cycloalkanone 2 at a tip of feed nozzle 1, which is preferably not lower than $8\times10^{-2}$ m/sec, more preferably not lower than $1\times10^{-1}$ m/sec and further more preferably not lower than 10 m/sec.

Mixing apparatus 3 in the present invention means a usual mixer used for a liquid-liquid mixing in a pipeline, and includes mixers such as jet mixer, static mixer, Banbury mixer, internal mixer, orifice mixer and impeller. Among them, a static mixer is preferable due to its simple structure and high mixing ability. Various types of static mixers are described in Chemical Engineering Handbook, Revised 6th edition, p 452, Maruzen Co., Ltd (1999), and a mixer such as manufactured by OHR Co., Ltd., which induces a compulsory swirl flow, may be used.

The number of said mixing apparatus 3 in the present invention is not restricted. That is, a certain number of said mixing apparatus may be connected in series or arranged in parallel in an aqueous solution of nitric acid 4. In the case of parallel arrangement, only a specified mixing apparatus may be installed with feed nozzles which are common to them, but it is preferable that each of said mixing apparatus has said feed nozzle. In the case of series connection, said feed nozzle may be installed only in the first said mixing apparatus or said feed nozzle may be independently installed in each of said mixing apparatus.

Figure 2:
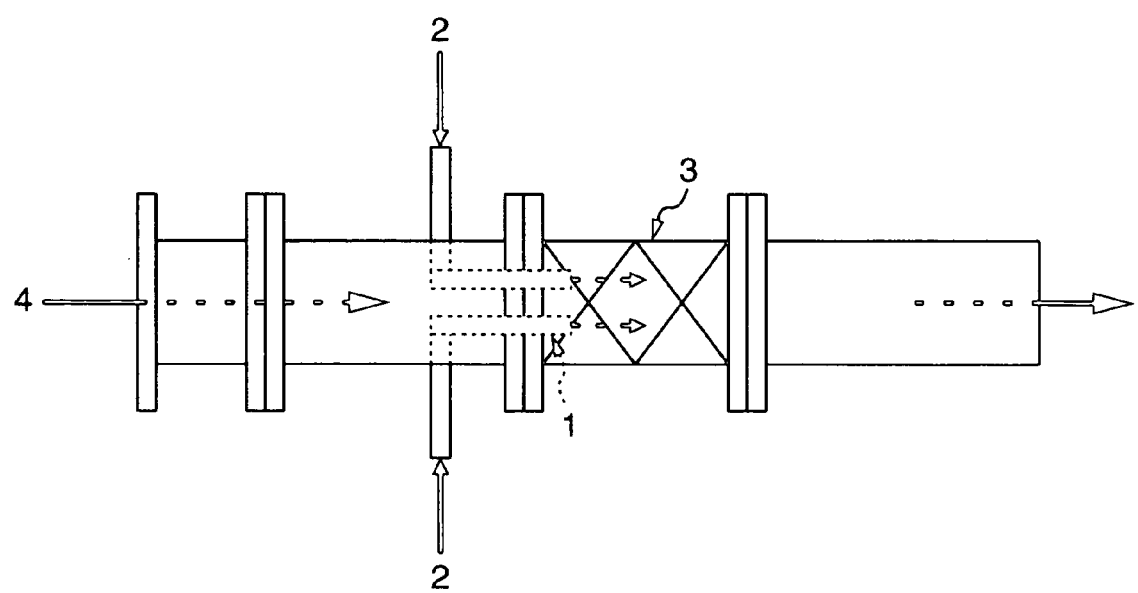
FIG. 2 is a schematic diagram of mixing apparatus in a method of the present invention.

Said feed nozzle 1 and said mixing apparatus 3 may be apart from each other, but the distance between them is preferably not longer than 10 mm, more preferably not longer than 5 mm. As shown in FIG. 2, said feed nozzle 1 may be completely incorporated in said mixing apparatus 3.

In the present invention, a ratio of a linear velocity of said cycloalkanol and/or cyclohexanone 2 at said feed nozzle 1 to a linear velocity of said aqueous solution of nitric acid in said mixing apparatus 3 is preferably not lower than $1\times10^{-2}$.

These requirements are aiming at an instantaneous mixing of cycloalkanol and/or cycloalkanone and an aqueous solution of nitric acid, however, shortening of the mixing time alone is not sufficient. It is important for a feed nozzle of cycloalkanol and/or cycloalkanone to enable feeding of cycloalkanol and/or cycloalkanone at the linear velocity not lower than $8\times10^{-2}$ m/sec.

In the present invention, the direction of a feed nozzle of cycloalkanol and/or cycloalkanone is preferably as parallel as possible to a flow of an aqueous solution of nitric acid. A T-tube may be used as a mixing apparatus, however, it is preferable to use a static mixer as a mixing apparatus by installing it so that a feed nozzle of said cycloalkanol and/or cycloalkanone becomes parallel to a flow of an aqueous solution of nitric acid. In any case, said cycloalkanol and/or cycloalkanone should be fed at the linear velocity not lower than $8\times10^{-2}$ m/sec.

In the present invention, it is preferable that a fluid comprising said aqueous solution of nitric acid, a reaction product from said cycloalkanol and/or cycloalkanone and said aqueous solution of nitric acid and unreacted portion of said cycloalkanol and/or cycloalkanone has a standard deviation not higher than 1.5° C. at the position where said fluid flows out by 2.5 sec from an outlet of said mixing apparatus. Standard deviation here is expressed by the following formula (1):

$$\text{Standard Deviation} = \sqrt{\frac{n\sum T^2 - (\sum T)^2}{n^2}} \quad (1)$$

n: Number of measuring points for temperature in radial direction of adiabatic reactor T(° C.): Temperature at each measuring points in radial direction of adiabatic reactor wherein, n is a number of measuring points for temperature. Distance among each measuring point is not longer than 5 mm. Temperature is measured at intervals not longer than 5 mm from a wall face of the reactor to a wall face in an opposite side in a radial direction. Thus, a reactor with a diameter of 100 mm gives 21 points for measuring the temperature.

For example, in the case where a diameter of said adiabatic reactor is 100 mm, a flow volume of fluid comprising said aqueous solution of nitric acid, reaction product from said cycloalkanol and/or cycloalkanone and said aqueous solution of nitric acid and unreacted portion of said cycloalkanol and/or cycloalkanone is 0.6 m³/hr and n is 21, the position apart from said mixing apparatus by 2.5 sec becomes the position apart from said mixing apparatus by 53 mm.

That is, in the case when said mixing apparatus is the one such as jet mixer, static mixer, Banbury mixer, internal mixer, orifice mixer and impeller, said position is the position apart from an outlet where the fluid flows out from said mixing apparatus by 53 mm.

A temperature profile in a radial direction is measured at the position with 21 measuring points.

In the case when said mixing apparatus is a T-tube or an injector, the starting point of the position apart from mixing apparatus by 2.5 sec is the position of a feed nozzle of said cycloalkanol and/or cycloalkanone in the downstream side of a flow of an aqueous solution of nitric acid.

Standard deviation exceeding 1.5° C. means that there is a generation of local high temperature portions causing a lower yield of an alkanedicarboxylic acid product. In a method for manufacturing an alkanedicarboxylic acid by oxidizing cycloalkanol and/or cycloalkanone with nitric acid, since the reaction is a sequential reaction, the selectivity of an alkanedicarboxylic acid increases if the former part of said sequential reaction is proceeded at low temperatures and the latter part at high temperatures. Moreover, said reaction is an exothermic reaction. If the standard deviation of temperature profile in a radial direction of said adiabatic reactor is not higher than 1.5° C., an ideal temperature profile in a flow direction for the above sequential reaction can be obtained because the temperature rises along the flow direction from an inlet to an outlet of said adiabatic reactor. On the contrary, said standard deviation exceeding 1.5° C. generates local high temperature portions in said reactor, which results in lowering the selectivity or yield.

In the present invention, in order to maintain the standard deviation in a temperature profile in the radial direction of said adiabatic reactor to not higher than 1.5° C. at the position where a fluid comprising said aqueous solution of nitric acid, the reaction product from said cycloalkanol and/or cycloalkanone and said aqueous solution of nitric acid and unreacted portion of said cycloalkanol and/or cycloalkanone flows out by 2.5 sec from an outlet of said mixing apparatus, certain number of said mixing apparatus may be placed in parallel as mentioned above. A temperature profile in the radial direction of said adiabatic reactor at the position apart from said mixing apparatus by 2.5 sec can be made flat by arranging certain number of said mixers in parallel in a reactor having a diameter of several meters.

Further, in the present invention, in order to maintain the standard deviation in a temperature profile in the radial direction of said adiabatic reactor to be not higher than 1.5° C. at the position where a fluid comprising said aqueous solution of nitric acid and the reaction product from said cycloalkanol and/or cycloalkanone and said aqueous solution of nitric acid and unreacted portion of said cycloalkanol and/or cycloalkanone flows out by 2.5 sec from an outlet of said mixing apparatus, a rectifier plate may also be installed at an outlet of said mixing apparatus. A rectifier plate in the present invention includes, for example, a porous plate and baffle tray or lip tray commonly used in a distillation tower. Said rectifier plate may be placed adjacent to said mixing apparatus or may be placed apart from said mixing apparatus by several centimeters to several meters. Two or more rectifier plates may be installed in a reactor, but it is preferable that the plate provides the above described temperature profile. In the case of two or more said rectifier plates being installed, the above described temperature profile is defined as a distribution at the position apart from said mixing apparatus by 2.5 sec.

Furthermore, in the present invention, it is preferable for a temperature profile in radial direction of said adiabatic reactor to have a standard deviation not higher than 1.5° C. even at the position apart from said mixing apparatus by the same distance as the radius of said adiabatic reactor.

In this case also, in the case when said mixing apparatus is a jet mixer, static mixer, Banbury mixer, internal mixer, orifice mixer, impeller, and the like, the starting point of the distance is defined as the position where a fluid flows out from said mixing apparatus, and in the case when said mixing apparatus is T-tube, it is defined as the position of a feed nozzle of cycloalkanol and/or cycloalkanone in the downstream side of a flow of an aqueous solution of nitric acid.

Moreover, in the present invention, it is more preferable that a fluid comprising said aqueous solution of nitric acid, a reaction product from said cycloalkanol and/or cycloalkanone and said aqueous solution of nitric acid and unreacted portion of said cycloalkanol and/or cycloalkanone, has a standard deviation not higher than 1.5° C. in a temperature profile in a radial direction of said adiabatic reactor at the position where said fluid flows out by 2.5 sec from an outlet of said mixing apparatus, and also a temperature profile in a radial direction of said adiabatic reactor has a standard deviation not higher than 1.5° C., at the position apart from said mixing apparatus by the same distance as the radius of said adiabatic reactor.

Standard deviation of a temperature profile in the present invention is important in a case of manufacturing an alkanedicarboxylic acid by oxidizing cycloalkanol and/or cycloalkanone with an aqueous solution of nitric acid in a commercial scale. With a so-called bench scale reactor, standard deviation of a temperature profile is, in many cases, smaller than 1.5° C. without using a rectifier plate or without installing a certain number of mixing apparatus in parallel, because a diameter of the reactor tube is as small as 10 mm around. However, in a commercial scale, some measures as described above are required to control the standard deviation to be not higher than 1.5° C. Commercial scale here means a scale using an adiabatic reactor with a diameter not smaller than 100 mm, preferably not smaller than 500 mm.

An adiabatic reactor in the present invention is defined as a pure adiabatic type reactor described in Kenji Hashimoto, "Industrial Reaction Apparatus" (Baihukan, 1984), p. 25–26. An one-stage type adiabatic reactor is preferable, but it may be a multi-stage adiabatic reactor of a mid-stage heat exchanging and multi-stage adiabatic type reactor, which is divided into several stages with heat exchangers being installed between each stage to provide or remove heat.

There is a method to use an isothermal reactor in a method for manufacturing an alkanedicarboxylic acid by oxidizing cycloalkanol and/or cycloalkanone with an aqueous solution of nitric acid. In this case, although a standard deviation of temperature profile naturally does not go higher than 1.5° C. because it is isothermal, a selectivity for an alkanedicarboxylic acid is lowered because the above described sequential reactions proceed at the same temperature. In addition, an adiabatic reactor can utilize a heat generated by reactions as the heat of concentrating the nitric acid, whereas an isothermal reactor requires a cooling apparatus to remove the reaction heat as well as the heat of concentrating the nitric acid separately.

In the present invention, an outlet temperature of said adiabatic reactor is not specially specified, but the temperature is preferably not lower than 80° C., and more preferably above 90° C. If an adiabatic reactor comprising a feed nozzle enabling to feed cycloalkanol and/or cycloalkanone at linear velocity not lower than $8 \times 10^{-2}$ m/sec and mixing apparatus is used, a yield of an alkanedicarboxylic acid obtained is not lowered but rather improved compared with the case of conventional technology, even if an outlet temperature of said adiabatic reactor becomes preferably not lower than 80° C., more preferably above 90° C. Therefore, as described above, by setting an outlet temperature of said adiabatic reactor preferably not lower than 80° C., more preferably above 90° C., it is possible not only to reduce an amount of nitric acid consumed by oxidizing cycloalkanol and/or cycloalkanone with nitric acid but also to raise the concentration of an alkanedicarboxylic acid formed in a reaction mixture at an outlet of said adiabatic reactor. This, in turn, makes it possible to lower a volume of total circulation flow of an aqueous solution of nitric acid circulating in a system, containing formed alkanedicarboxylic acid, then enables to reduce the loads of a crystallizer and a concentration tower.

As an example, the cases where the outlet temperature of said adiabatic reactor are 90° C. and 75° C. are now considered using adipic acid as the alkanedicarboxylic acid. If 10° C. is taken as an allowance for solubility to prevent a deposition of adipic acid in pipelines or valves, the solution can contain adipic acid of about 22% by weight at the maximum, equivalent to the solubility at 80° C., in the case of an outlet temperature of 90° C., whereas it can contain only about 15% by weight, equivalent to the solubility at 65° C., in the case of an outlet temperature of 75° C. This means that an amount of reaction mixture to be introduced from a reaction system to a crystallization system, that is, total circulation volume of an aqueous solution of nitric acid, becomes 22/15=1.5 times in order to obtain the same production amount of adipic acid. Reduction of total circulation volume of an aqueous solution of nitric acid contributes to lower loads of a crystallizer and a concentration tower. Furthermore, a higher concentration of adipic acid reduces the energy required for crystallization in a crystallizer.

In addition, according to a method of the present invention, it is not necessary to increase the circulation volume of nitric acid in the reaction system to maintain a yield of an alkanedicarboxylic acid at an outlet temperature of said adiabatic reactor of preferably not lower than 80° C., more preferably above 90° C. In a conventional technology, when an outlet temperature of reactor was set at above 90° C., a weight ratio of a circulation volume of nitric acid in a reaction system to reaction components had to be greatly increased so as not less than 200 in order to maintain a yield of an alkane dioic acid. By using an adiabatic reactor comprising a feed nozzle enabling to feed cycloalkanol and/or cycloalkanone at a linear velocity not lower than $8 \times 10^{-2}$ m/sec and a mixing apparatus, a yield of an alkane dioic acid can be raised even under such conditions as a weight ratio of a circulation volume of nitric acid in a reaction system to reaction components smaller than 200 and an outlet temperature of said adiabatic reactor above 90° C.

The present invention can comprise oxidation reaction with nitric acid, separating nitrogen oxide, dinitrogen oxide, nitrogen dioxide and nitrous acid from the reaction mixture coming out from said adiabatic reactor, then concentrating said reaction mixture until obtaining a concentration of nitric acid nearly equivalent to the concentration of nitric acid at an inlet of reactor by evaporating water formed in said adiabatic reactor from said reaction mixture, separating said alkanedicarboxylic acid from a part of the concentrated reaction mixture, concentrating nitric acid in the mother liquid in another concentrating system, joining said mother liquid and the remaining part of said concentrated reaction mixture together, mixing the joined mixture with a fresh aqueous solution of nitric acid, and returning the mixture to a reactor.

Concentration of nitric acid nearly equivalent to the concentration at an inlet of a reactor here means, for example, the concentration within a concentration of nitric acid at an inlet of a reactor—5.0% by weight.

The present invention will be explained in detail in accordance with the drawings illustrating an embodiment in the case when a method of the present invention is applied to an engineering use.

Figure 3:
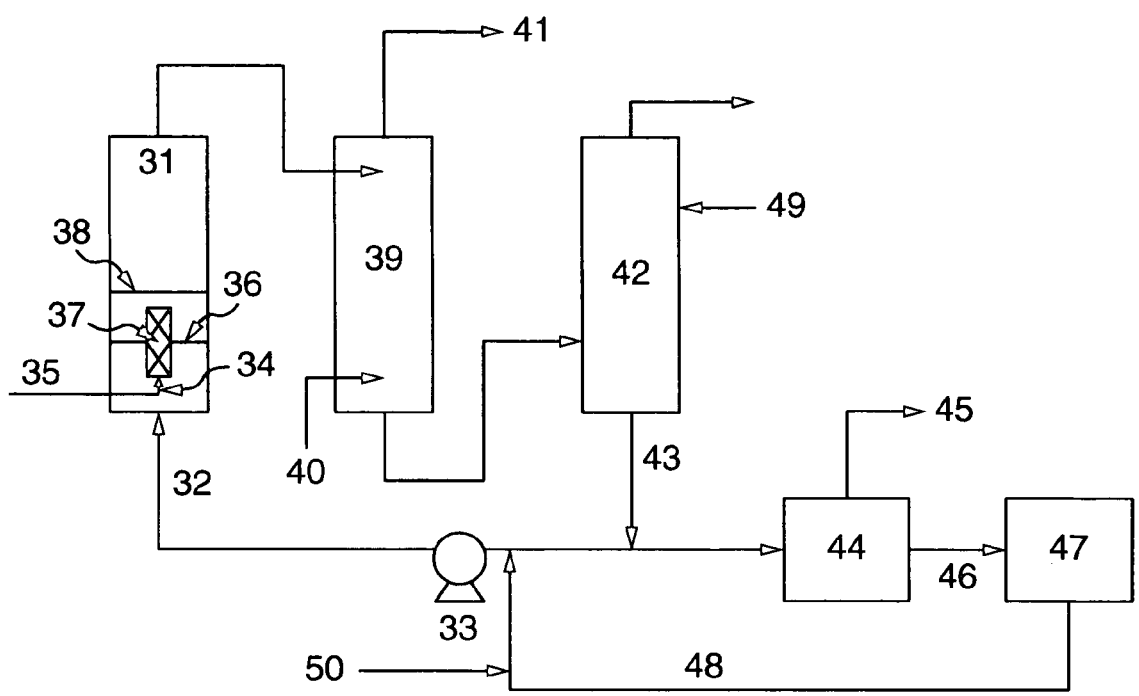
FIG. 3 is a schematic diagram showing an embodiment of reaction system, crystallization system and concentration system when a method of the present invention is applied to an engineering use.

In FIG. 3, an adiabatic reactor is shown as (31). An aqueous solution of nitric acid, as a circulation flow in a reaction system (32), is sent from the bottom of said reactor (31) via a pump (33). Cycloalkanone and/or cycloalkanol (35) is fed by a feed nozzle (34) enabling to feed cycloalkanol and/or cycloalkanone at a linear velocity not lower than $8 \times 10^{-2}$ m/sec. Said circulation flow in a reaction system (32) and said cycloalkanone and/or cycloalkanol (35) are instantaneously mixed by a mixing apparatus (37) supported by a supporting plate (36). A porous plate (38) is installed at the position apart from an outlet of said mixing apparatus (37) by several hundreds mm. Reaction product at temperature higher than 90° C., coming out from said reactor (31) is introduced to a stripper tower (39), where air (40) is fed to strip components such as nitrogen oxide, nitrous acid, nitrogen dioxide and dinitrogen oxide (41). Stripped gas is absorbed in an absorption tower and recovered as nitric acid. A decomposition tower for dinitrogen oxide, global warming gas, may be installed between said stripper tower (39) and said absorption tower. Reaction product coming out from said stripper tower (39) is fed to a concentration tower (42) for nitric acid. Said concentration tower (42) for nitric acid is operated under a reduced pressure, where a part of reaction heat is utilized for concentrating nitric acid. Water or cleaning water (49) used in a subsequent crystallization process is showered to recover nitric acid. An aqueous solution of nitric acid (43) concentrated in said concentration tower (42) to a concentration nearly equivalent to the concentration in a reaction zone forms circulation flow in reaction system (32) through a pump (33). A part of bottom liquid (43) of said concentration tower (42) for nitric acid is taken out from the reaction system and becomes a product (45) via crystallization process (44). Mother liquid (46) coming out from crystallization process (44) is concentrated via another concentration system (47) and forms a total circulation flow (48). Said total circulation flow (48) is mixed with the above mentioned circulation flow in the reaction system (32). Fresh nitric acid (50) is fed to maintain a concentration of nitric acid constant in said circulating aqueous solution of nitric acid in the reaction system at an inlet of said adiabatic reactor.

Said alkanedicarboxylic acid remaining unseparated is contained in aqueous solution of nitric acid in the above described circulation flow in a reaction system (32) and a total circulation flow (48). Concentration of said alkanedicarbonylic acid contained in said aqueous solution of nitric acid is 5 to 40%, however, 5 to 30% is preferable because too high concentration may reach a limit of solubility and requires warming up of said aqueous solution of nitric acid to prevent a deposition of crystals in pipelines or intermediate tanks.

In the present invention, a concentration of said alkanedicarboxylic acid, contained in a circulation flow in the reaction system and a total circulation flow, can be raised because an outlet temperature of said adiabatic reactor can be raised up to the temperature preferably not lower than 80° C., more preferably above 90° C.

The present invention will be explained using Examples and Comparative Examples below.

Hereinbelow, yields of an alkane dioic acid are compared between the cases of feeding a reactant, cycloalkanol and/or cycloalkanone, at linear velocities of not lower than $8 \times 10^{-2}$ m/sec and not higher than $8 \times 10^{-2}$ m/sec, under the same mixing time. Mixing time here means a time until the color of phenolphthalein disappears, when NaOH and $H_2SO_4$ are mixed using phenolphthalein as a tracer.

Also hereinbelow, a position where a fluid comprising said aqueous solution of nitric acid, reaction product from said cycloalkanol and/or cycloalkanone and said aqueous solution of nitric acid and unreacted portion of said cycloalkanol and/or cycloalkanone, flows out from said mixing apparatus by 2.5 sec is simply expressed as a position at 2.5 sec.

EXAMPLE 1

A reactor which had a mixing part of a length of 191 mm with 4 elements of static mixers each of an inside diameter of 30 mm made by Noritake Co., Ltd. and had a length of 686 mm, inclusive of the static mixers, was provided. Into said static mixer, 0.004N of NaOH colored with phenolphthalein was charged. As shown in FIG. 1, two feed nozzles with an inside diameter of 1 mm were installed in a just upstream side of said static mixer, and 1N of $H_2SO_4$ was fed from said feed nozzles. A distance to the position where a color of phenolphthalein disappeared was converted to a time and defined as a mixing time. NaOH at the rate of 0.95 [lit/hr] and $H_2SO_4$ at the rate of 102 [lit/hr] were passed and a mixing time was determined to be 1.1 sec.

Then, an oxidation reaction of cyclohexanol with nitric acid was conducted using the same static mixer and feed nozzles. More concretely, 54.6% by weight of aqueous solution of nitric acid containing 0.5% by weight of Cu and 0.05% by weight of V was passed to said static mixer at a rate of 133 kg/hr at 73.8° C., and cyclohexanol was fed at a rate of 0.9 kg/hr for 5 hrs from said feed nozzles. An outlet temperature of said reactor was 91.8° C. A mixing time in this case was 1.1 sec and a linear velocity of cyclohexanol was 0.17 m/sec. A liquid sample was collected at an outlet of reactor, and a yield of adipic acid was determined to be 94.1% by mol to the theoretical value. An amount of nitric acid consumed was 0.967 kg-$HNO_3$/kg-adipic acid. A temperature profile at the position apart from the mixer by 15 mm was measured, and a standard deviation of temperature was 0.50° C.

COMPARATIVE EXAMPLE 1

A reactor with a length of 650 mm comprising a T-tube having a mixing part with an inside diameter of 16.1 mm and a length of 250 mm was provided. Into one end of said T-tube, 0.004N of NaOH colored with phenolphthalein was charged at the rate of 0.738 [lit/hr], and 1N of $H_2SO_4$ was fed at the rate of 115 [lit/hr] from the other end. A distance to the position where a color of phenolphthalein disappeared was converted to a time and a mixing time was determined to be 1.1 sec.

Then, an oxidation reaction of cyclohexanol with nitric acid was conducted using the same T-tube. More concretely, 55.0% by weight of aqueous solution of nitric acid containing 0.5% by weight of Cu and 0.05% by weight of V was passed to said T-tube at a rate of 150 kg/hr at 75.6° C., and cyclohexanol was fed at the rate of 0.7 kg/hr for 5 hrs from said feed nozzle. An outlet temperature of said reactor was 91.0° C. A mixing time in this case was 1.1 sec and a linear velocity of cyclohexanol was 0.001 m/sec. A liquid sample was collected at an outlet of reactor, and a yield of adipic acid was determined to be 91.6% by mol. An amount of nitric acid consumed was 1.018 kg-$HNO_3$/kg-adipic acid. A temperature profile at the position apart from the mixer by 8 mm was measured, and a standard deviation of temperature was 0.90° C.

Although the average temperature and the mixing time were the same as those in Example 1, the yield of adipic acid in Comparative Example 1 was lower than that in Example 1, because the linear velocity of cyclohexanol was not higher than $8 \times 10^{-2}$ m/sec.

EXAMPLE 2

Using a T-tube which has a inside diameter of 10 mm but a inside diameter of 2 mm only for feeding side of cyclohexanol, a mixing time was measured by the same method as in Comparative Example 1 to be 1.1 sec.

Then, an oxidation reaction of cyclohexanol with nitric acid was conducted using the same T-tube. More concretely, 55.3% by weight of aqueous solution of nitric acid containing 0.5% by weight of Cu and 0.05% by weight of V was passed to said T-tube at the rate of 132 kg/hr at 78.1° C., and cyclohexanol was fed at the rate of 0.9 kg/hr for 5 hrs from said feed nozzle. An outlet temperature of said reactor was 91.3° C. A mixing time in this case was 1.1 sec and a linear velocity of cyclohexanol was 0.09 m/sec. A liquid sample was collected at an outlet of reactor, and a relative molar yield of adipic acid was determined to be 94.0% by mol. An amount of nitric acid consumed was 0.968 kg-$HNO_3$/kg-adipic acid. A temperature profile at the position apart from the mixer by 5 mm was measured, and a standard deviation of temperature was 0.70° C. A standard deviation of temperature at the position apart from the mixer by 2.5 sec was 0.50° C.

Although the average temperature and the mixing time were the same as those in Comparative Example 1 with the same T-tube type mixing apparatus, the yield of adipic acid in Example 2 was as high as in Example 1, because the linear velocity of cyclohexanol in Example 2 was not lower than $8 \times 10^{-2}$ m/sec.

EXAMPLE 3

Into a reactor with a length of 700 mm, which comprises a static mixer having a mixing part with an inside diameter of 12 mm, 1N of $H_2SO_4$ was passed at the rate of 99 [lit/hr]. Two feed nozzles with a hole of 1 mm were installed in a just upstream side of said static mixer, and 0.004N of NaOH colored with phenolphthalein was fed from said feed nozzles at the rate of 0.967 [lit/hr]. A mixing time was determined by the same method as in Example 1 to be 0.07 sec.

Then, an oxidation reaction of cyclohexanol with nitric acid was conducted using the same static mixer and feed nozzles. More concretely, 55.3% by weight of aqueous solution of nitric acid containing 0.5% by weight of Cu and 0.04% by weight of V was passed to said static mixer at the rate of 130 kg/hr at 78.4° C., and cyclohexanol was fed at the rate of 0.917 kg/hr from said feed nozzles. Thus, a weight ratio of circulation flow in the reaction system to cyclohexanol was 142. A mixing time was 0.07 sec and a linear velocity of cyclohexanol was 0.17 m/sec. A temperature profile in a radial direction at the position apart from an outlet of the static mixer by 6 mm was measured, and a standard deviation was 0.60° C. A temperature at an outlet of the reactor in this case was 91.2° C.

Gas coming out from an outlet of reactor was introduced to a stripper tower, where nitrogen oxide, nitrogen dioxide, dinitrogen oxide and nitrous acid were stripped with air, then concentrated in a concentration tower. Bottom temperature of said concentration tower was about 80° C. and concentration of adipic acid in an aqueous solution of nitric acid coming out from the bottom of the tower was 21% by weight. A part of said aqueous solution of nitric acid was taken out from the system and the remaining aqueous solution of nitric acid was returned to the reactor as a circulation flow in the reaction system. Yield of adipic acid obtained was 96.2% by weight to the theoretical value. Fresh nitric acid was added so that a concentration of nitric acid at an inlet of the reactor became 55.3% by weight. An amount of nitric acid consumed per adipic acid was 806 [kg/T-adipic acid].

COMPARATIVE EXAMPLE 2

Into a reactor with a length of 800 mm, which comprises an injector having a mixing part with an inside diameter of 11 mm, 1N of $H_2SO_4$ was passed at the rate of 99 [lit/hr]. From said injector, 0.004N of NaOH colored with phenolphthalein was fed from said feed nozzles at the rate of 0.503 [lit/hr]. A mixing time was determined by the same method as in Example 1 to be 0.05 sec.

Then, an oxidation reaction of cyclohexanol with nitric acid was conducted using the same injector. More concretely, 60% by weight of aqueous solution of nitric acid containing 0.5% by weight of Cu and 0.04% by weight of V was passed to said static mixer at the rate of 130 kg/hr at 60° C. Cyclohexanol was fed at the rate of 0.477 kg/hr perpendicularly to a flow of an aqueous solution of nitric acid by the injector with an inside diameter of 11 mm, which enabled to dissolve cyclohexanol to transparent state after 0.05 sec. Linear velocity of cyclohexanol at this condition was 0.002 m/sec. Standard deviation of temperature profile in radial direction at the position apart from the injector by 6 mm was 0.70° C. The reaction mixture was removed from the reactor at 70° C. and introduced to a stripper tower, where nitrogen oxide, nitrogen dioxide, dinitrogen oxide and nitrous acid were stripped with air and sent to a concentration tower. A concentration of nitric acid was raised up to about 56% by weight in the concentration tower. Bottom temperature of the concentration tower was about 55° C. and concentration of adipic acid in an aqueous solution of nitric acid coming out from the bottom of the tower was 9% by weight. A part of said aqueous solution of nitric acid was taken out from the system and the remaining aqueous solution of nitric acid was returned to the reactor as a circulation flow in the reaction system. Yield of adipic acid obtained was 95.0% by weight to the theoretical value. Fresh nitric acid was added so that a concentration of nitric acid at an inlet of reactor became 60% by weight. An amount of nitric acid consumed per adipic acid was 840 [kg/T-adipic acid].

An amount of nitric acid consumed per adipic acid was higher than that in Example 2 because reaction temperature was low. Yield of adipic acid was lower notwithstanding a lower reaction temperature and a shorter mixing time. Furthermore, a concentration of adipic acid in an aqueous solution of nitric acid coming out from the bottom of the tower to crystallization system was lower because the reaction temperature was lower. An amount of an aqueous solution of nitric acid to be taken out was 21/9=2.3 times in order to obtain the same amount of adipic acid as in Example 2. This means that a load to crystallization system and subsequent concentration system becomes large in a commercial process.

COMPARATIVE EXAMPLE 3

To a continuous type stainless steel isothermal apparatus, 50% by weight of an aqueous solution of nitric acid containing 0.5% by weight of Cu and 0.04% by weight of V was fed at the rate of 130 kg/hr at 11 0° C. together with cyclohexanol at the rate of 0.13 kg/hr, after being mixed in T-tube with an inside diameter of 13 mm. Linear velocity of cyclohexanol at this condition was 0.0003 m/sec and mixing time was 1.05 sec.

A part of reaction mixture was taken out to crystallization system and the remaining part was returned to reaction system. Weight ratio of this circulating aqueous solution of nitric acid in reaction system to cyclohexanol was 1000. Yield of adipic acid obtained was 94.1% by weight of the theoretical value. An amount of nitric acid consumed per adipic acid was 807 [g/T-adipic acid].

Yield of adipic acid obtained was lower because linear velocity of cyclohexanol was lower than in Example 2. Furthermore, load to the reactor or a circulation pump and pipelines was 7 times larger because circulating flow in reaction system was as much as 7 times (1000:142).

EXAMPLE 4

To a static mixer with an inside diameter of 80 mm, 1N of $H_2SO_4$ was fed at the rate of 123 m³/hr. Two feed nozzles each having two holes with a diameter of 2.4 mm, are installed just upstream side of said static mixer, by which 0.004N of NaOH, colored with phenolphthalein, was fed at the rate of 1.2 m³/hr. Mixing time, determined by the same method as in Example 1, was 0.05 sec.

To an adiabatic reactor having an inside diameter of 1000 mm and a height of 10000 mm, 53.6% by weight of circulating aqueous solution of nitric acid in reaction system containing 0.5% by weight of Cu and 0.04% by weight of V, was fed at the rate of 780 T/H at 78.2° C. Five static mixers each with an inside diameter of 80 mm were installed in an adiabatic reactor in parallel to a flow of an aqueous solution of nitric acid, and to each of the mixers, two feed nozzles with an inside diameter of 10 mm, each having two holes of 2.4 mm, were installed nearly parallel to a flow of an aqueous solution of nitric acid. Cyclohexanol was fed at the rate of 5.6 T/H from said feed nozzles. Thus weight ratio of a circulation flow in reaction system to cyclohexanol was 138. Mixing time was 0.05 sec and linear velocity of cyclohexanol was 18.3 m/sec. A porous plate was set at the position apart from an outlet of the static mixer by 300 mm. Standard deviation of temperature, measured by a temperature profile in a radial direction at the position of 2.5 sec from an outlet of the static mixer, was 1.00° C. Standard deviation of temperature at the position apart from an outlet of the static mixer by 500 mm was also 1.00° C. Temperature at an outlet of the adiabatic reactor was 95° C.

Gas coming out from an outlet of reactor was introduced to a stripper tower, where nitrogen oxide, nitrogen dioxide, dinitrogen oxide and nitrous acid were stripped with air and a concentration of nitric acid was raised up to about 40% by weight in a concentration tower under the top pressure of 20 KPa. Bottom temperature of said concentration tower was about 80° C. and concentration of adipic acid in an aqueous solution of nitric acid coming out from the bottom of the tower was 21% by weight. A part of said aqueous solution of nitric acid was sent to crystallization process and the remaining aqueous solution of nitric acid was returned to the adiabatic reactor as a circulation flow in reaction system. Adipic acid was obtained by crystallization and purification of an aqueous solution of nitric acid thus taken out and sent to crystallization process, using usual methods. Yield of adipic acid obtained was 95.8% by weight of the theoretical value. Mother liquid coming out from crystallization process was concentrated by another concentration process and returned to the above described circulation flow in reaction system. Fresh nitric acid was added so that a concentration of nitric acid at an inlet of adiabatic reactor became 53.6% by weight. An amount of nitric acid consumed per adipic acid was 800 [kg/T-adipic acid].

EXAMPLE 5

A 55.0% by weight of circulating aqueous solution of nitric acid in reaction system, containing 0.5% by weight of Cu and 0.04% by weight of V, was fed at the rate of 780 T/H at 77° C. and cyclohexanol from a feed nozzle at the rate of 5.6 T/H, by the same method as in Example 4 except for not installing a porous plate. Standard deviation of temperature, measured by a temperature profile in a radial direction at the position of 2.5 sec from an outlet of the static mixer, was 2.50° C. and temperature at an outlet of the adiabatic reactor was 95° C. Standard deviation of temperature at the position apart from an outlet of the static mixer by 500 mm was 2.44° C. Yield of adipic acid obtained was 95.1% by weight of the theoretical value.

Yield of adipic acid was lower than that in Example 4 because standard deviation was not lower than 1.5° C.

EXAMPLE 6

A 55.0% by weight of circulating aqueous solution of nitric acid in reaction system, containing 0.5% by weight of Cu and 0.04% by weight of V, was fed at the rate of 780 T/H and cyclohexanol by a feed nozzle at the rate of 5.6 T/H, by the same method as in Example 4 except for temperature at an inlet of the adiabatic rector was set at 68° C. Standard deviation of temperature, measured by a temperature profile in a radial direction at the position at 2.5 sec from an outlet of the static mixer, was 1.00° C. and temperature at an outlet of the adiabatic reactor was 85° C. Yield of adipic acid obtained was 96.6% by weight of the theoretical value, a little better than that in Example 4, however, amount of nitric acid consumed per adipic acid was 834 [kg-nitric acid/T-adipic acid], which was higher than 800 [kg-nitric acid/T-adipic acid] in Example 4, because of the lower temperature. Furthermore, gas from an outlet of the reactor was introduced to an stripper tower, where nitrogen oxide, nitrogen dioxide, dinitrogen oxide and nitrous acid were stripped with air, then a concentration of nitric acid was raised up to about 40% by weight in a concentration tower operated under the top pressure of 20 KPa. Bottom temperature of the concentration tower was about 70° C. and concentration of adipic acid in an aqueous solution of nitric acid coming out from the bottom of the tower was 15% by weight. Amount of total circulation of an aqueous solution of nitric acid was 1.4 times as much as that in Example 4, because of lower adipic acid concentration than that in Example 4, and a load to crystallization in a subsequent process was also increased by 1.4 times.

COMPARATIVE EXAMPLE 4

A reactor with a length of 650 mm comprising a mixing part using a T-tube with an inside diameter of 2.9 mm and a length of 250 mm was provided. Distance to the position where color of phenolphthalein disappeared was converted to time by the same method as in Comparative Example 1, and mixing time was determined to be 0.01 sec.

Then, an oxidation reaction of cyclohexanol with nitric acid was conducted using the same T-tube. More concretely, 55.0% by weight of aqueous solution of nitric acid containing 0.5% by weight of Cu and 0.05% by weight of V was passed to said T-tube at the rate of 150 kg/hr at 78.4° C., and cyclohexanol was fed at the rate of 0.7 kg/hr for 5 hrs from said feed nozzle. An outlet temperature of said reactor was 91.0° C. A mixing time in this case was 0.01 sec and a linear velocity of cyclohexanol was 0.03 m/sec. A liquid sample was collected at an outlet of reactor, and a yield of adipic acid was determined to be 94.7% by weight. An amount of nitric acid consumed was 0.915 kg-$HNO_3$/kg-adipic acid. A temperature profile at the position apart from the mixer by 2.5 sec was measured, and a standard deviation of temperature was 0.80° C.

Although the mixing time was shorter than that in Example 3, a yield of adipic acid was lower, because the linear velocity of cyclohexanol in Comparative Example 4 was not higher than $8 \times 10^{-2}$ m/sec.

TABLE 1

|  |  | Example 1 | Example 2 | Comparative Example 1 | Example 3 | Comparative Example 2 | Comparative Example 3 | Example 4 | Example 5 | Example 6 | Comparative Example 4 |
|---|---|---|---|---|---|---|---|---|---|---|---|
| Inlet Temp. | [° C.] | 73.8 | 78.1 | 75.6 | 78.4 | 60 | Isothermal Type Reactor | 78.2 | 77 | 68.2 | 78.4 |
| Outlet Temp. | [° C.] | 91.8 | 91.3 | 91 | 91.2 | 70 | Isothermal Type Reactor | 95 | 95 | 85 | 91 |
| Average Temp. | [° C.] | 82.8 | 84.7 | 83.3 | 84.8 | 65 | 110 | 86.6 | 87 | 76.6 | 84.7 |
| Diameter of Reactor | [mm] | 30 | 10 | 16.1 | 12 | 11 | Isothermal Type Reactor | 1000 | 1000 | 1000 | 2.9 |
| Length of Reactor | [mm] | 686 | 650 | 650 | 700 | 800 | Isothermal Type Reactor | 10000 | 10000 | 10000 | 650 |
| Mixer |  | Static Mixer | T-Tube | T-Tube | Static Mixer | Injector | T-Tube | 5 Static Mixers | 5 Static Mixers | 5 Static Mixers | T-Tube |
| Inside Diameter of Mixer | [mm] | 30 | 10 | 16.1 | 12 | 11 | 13 | 80 | 80 | 80 | 2.9 |
| Mixing Time | [sec] | 1.1 | 1.1 | 1.1 | 0.07 | 0.05 | 1.05 | 0.05 | 0.05 | 0.05 | 0.01 |
| Inside Diameter of KA-Oil Feed | [mm] | 1 | 2 | 16.1 | 1 | 11 | 11 | 2.4 | 2.4 | 2.4 | 2.9 |
| Linear Velocity of KA-Oil | [m/sec] | 0.17 | 0.09 | 0.001 | 0.17 | 0.002 | 0.0003 | 18.3 | 18.3 | 18.3 | 0.03 |
| Conc. of Nitric acid | [wt %] | 54.6 | 55.3 | 55.0 | 55.3 | 60.0 | 50.0 | 53.6 | 55.0 | 55.0 | 55.1 |
| KA-Oil |  | NOL | NOL | NOL | NOL | NOL | NOL | NOL | NOL | NOL | NOL |
| Conc. of Cu | [wt %] | 0.5 | 0.5 | 0.5 | 0.5 | 0.5 | 0.5 | 0.5 | 0.5 | 0.5 | 0.5 |
| Conc. of V | [wt %] | 0.05 | 0.05 | 0.05 | 0.04 | 0.04 | 0.04 | 0.04 | 0.04 | 0.04 | 0.04 |
| Amount of Circulating Nitric acid | [T/hr] | 0.133 | 0.132 | 0.15 | 0.13 | 0.13 | 0.13 | 780 | 780 | 780 | 0.15 |
| Amount of KA-Oil | [kg/hr] | 0.9 | 0.9 | 0.7 | 0.917 | 0.477 | 0.13 | 5660 | 5660 | 5660 | 0.7 |
| Amount of Circulating Nitric acid/KA-Oil | [—] | 148 | 147 | 214 | 142 | 273 | 1000 | 138 | 138 | 138 | 214 |
| Yield of ADA |  | 94.1 [mol %] | 94.0 [mol %] | 91.6 [mol %] | 96.2 [wt %] | 95.0 [wt %] | 94.1 [wt %] | 95.8 [wt %] | 95.1 [wt %] | 96.6 [wt %] | 94.7 [wt %] |
| Consumption of Nitric acid | [kg NA/T-ADA] | 967 | 968 | 1018 | 806 | 840 | 807 | 800 | 806 | 834 | 915 |
| Conc. of ADA at Outlet of Reactor | [wt %] | 20 | 19 | 19 | 21 | 9 | 30 | 21 | 21 | 15 | 18 |
| Porous Plate |  |  | No |  |  | No |  | Yes | No | Yes | No |
| Temperature standard Deviation at a Position of 2.5 sec [° C.] |  | 0.42 | 0.55 | 0.65 | 0.50 | 0.55 | Isothermal | 1.00 | 2.50 | 1.00 | 0.80 |
| Temperature Standard Deviation at the Same Distance as Radius [° C.] |  | 0.50 | 0.70 | 0.90 | 0.60 | 0.70 | Isothermal | 1.00 | 2.44 | 0.98 | 1.20 |

KA-Oil: Cycloalkanone and/or cycloalkanol

INDUSTRIAL APPLICABILITY

According to a method of the present invention, in a method for manufacturing an alkanedicarboxylic acid by oxidizing cycloalkanol and/or cycloalkanone with an aqueous solution of nitric acid using an adiabatic reactor, it is possible to improve a yield of an alkanedicarboxylic acid, reduce an amount of nitric acid required, reduce an air volume in a stripper tower, lower an amount of total circulation flow of an aqueous solution of nitric acid and thus lower loads of a crystallizer and a concentration tower, without increasing an amount of circulation flow of nitric acid in a reaction system more than required, irrespective of the temperature of said adiabatic reactor.

The invention claimed is:

1. A method for preparing an alkanedicarboxylic acid by oxidizing cycloalkanol and/or cycloalkanone with an aqueous solution of nitric acid, which comprises mixing cycloalkanol and/or cycloalkanone with an aqueous solution of nitric acid using an adiabatic reactor comprising a feed nozzle and a mixing apparatus, wherein said cycloalkanol and/or cycloalkanone is fed by said feed nozzle at a linear velocity of not lower than $8 \times 10^{-2}$ m/sec.

2. A method according to claim 1, wherein an outlet temperature of said adiabatic reactor is above 90° C.

3. A method according to claim 1 or claim 2, wherein a fluid comprising said aqueous solution of nitric acid, a reaction product from said cycloalkanol and/or cycloalkanone and said aqueous solution of nitric acid and unreacted portion of said cycloalkanol and/or cycloalkanone have a standard deviation of a temperature profile in a radial direction of said adiabatic reactor of not higher than 1.5° C. at the position where said fluid flows out from an outlet of said mixing apparatus in 2.5 sec.

4. A method according to claim 1 or claim 2, wherein a standard deviation of a temperature profile in a radial direction of said adiabatic reactor is not higher than 1.5° C. at a position apart from said mixing apparatus by the same distance as a radius of said adiabatic reactor.

5. A method according to claim 1, wherein a fluid comprising said aqueous solution of nitric acid, a reaction product from said cycloalkanol and/or cycloalkanone and said aqueous solution of nitric acid and an unreacted portion of said cycloalkanol and/or cycloalkanone have a standard deviation of a temperature profile in a radial direction of said adiabatic reactor of not higher than 1.5° C. at the position where said fluid flows out from an outlet of said mixing apparatus in 2.5 sec, and a standard deviation of a temperature profile in a radial direction of said adiabatic reactor of not higher than 1.5° C. at a position apart from an outlet of said mixing apparatus by the same distance as a radius of said adiabatic reactor.

6. A method according to claim 1, wherein said aqueous solution of nitric acid is the one which is returned to the reactor after separating nitrogen oxide, dinitrogen oxide, nitrogen dioxide and nitrous acid from the reaction mixture coming out from said adiabatic reactor after the nitric acid oxidation reaction, then concentrating said reaction mixture until obtaining a concentration of nitric acid nearly equivalent to the concentration of nitric acid at an inlet of the reactor by evaporating water formed in said adiabatic reactor from said reaction mixture, separating said alkanedicarboxylic acid from a part of said concentrated reaction mixture, concentrating nitric acid in a mother liquid in another concentrating system, joining said mother liquid and a remaining part of said concentrated reaction mixture together, and mixing the joined mixture with a fresh aqueous nitric acid solution.

7. A method according to claim 1, wherein said cycloalkanol and/or cycloalkanone is cyclohexanol and/or cyclohexanone and said alkanedicarboxylic acid to be manufactured is adipic acid.

8. A method according to claim 1, wherein the mixing is essentially instantaneous.

* * * * *